US 7,887,490 B2

(12) United States Patent
Danehorn et al.

(10) Patent No.: US 7,887,490 B2
(45) Date of Patent: Feb. 15, 2011

(54) METHOD AND DEVICE FOR REMOVING RESPIRATORY ARTEFACTS FROM MEASURED BLOOD PRESSURE DATA

(75) Inventors: Kenneth Danehorn, Vaxholm (SE);
Fredrik Gustafsson, Linköping (SE);
Martin Wikström, Solna (SE)

(73) Assignee: Siemens Aktiengesellscahft, Munich (KR)

( * ) Notice: Subject to any disclaimer, the term of this patent is extended or adjusted under 35 U.S.C. 154(b) by 1175 days.

(21) Appl. No.: 11/529,679

(22) Filed: Sep. 28, 2006

(65) Prior Publication Data

US 2007/0073170 A1    Mar. 29, 2007

(30) Foreign Application Priority Data

Sep. 29, 2005   (EP)   .................................. 05021339

(51) Int. Cl.
*A61B 5/08* (2006.01)
(52) U.S. Cl. .................. 600/485; 600/484; 600/301; 600/481; 600/486
(58) Field of Classification Search .................. 600/300, 600/301, 481–486, 500, 508–509, 529, 532
See application file for complete search history.

(56) References Cited

U.S. PATENT DOCUMENTS 5,375,604 A    12/1994   Kelly et al.
5,540,727 A *  7/1996   Tockman et al. ............... 607/18
5,758,652 A *  6/1998   Nikolic ........................ 600/487

FOREIGN PATENT DOCUMENTS

| EP | 0 563 425 A1 | 10/1993 |
| EP | 0 850 592 A2 | 7/1998 |
| WO | WO 03/055395 A1 | 7/2003 |

OTHER PUBLICATIONS

Georgios D. Mitsis, Marc J. Poulin, Peter A Robbins and Vasilis Z. Marmarelis, "Nonlinear Multivariate Analysis of Dynamic Cerebral Blood Flow Regulation in Humans", IEEE 2002, Proceedings of the Second Joint EMBS/BMES Conference, Houston, TX, USA, Oct. 23, 26, 2002, pp. 1341-1342.
S.A. Hoeksel, J.A. Blom, J.R. Jansen and J.J. Schreuder, "Correction for respiration artifact in pulmonary blood pressure signals of ventilated patients", Journal of Clinical Monitoring, Sep. 12, 1996, pp. 397-403, Retrieved from Internet on Sep. 28, 2005.

* cited by examiner

*Primary Examiner*—Robert L Nasser
*Assistant Examiner*—Michael D'Angelo

(57) ABSTRACT

The invention relates to a method and a device for removing respiratory artefacts in invasive blood pressure measurements. The level of $CO_2$ in the expired air is monitored during blood pressure measurement and used to approximate and remove the respiratory artifacts. In one embodiment, the respiratory frequency from the respiratory signal is extracted by identifying the end-tidal $CO_2$ level for each breath. A model is derived for the respiratory artifacts using the respiratory frequency, and the model is subtracted from the measured blood pressure data.

9 Claims, 4 Drawing Sheets

METHOD AND DEVICE FOR REMOVING RESPIRATORY ARTEFACTS FROM MEASURED BLOOD PRESSURE DATA

CROSS REFERENCE TO RELATED APPLICATIONS

This application claims priority of European application No. 05021339.6 filed Sep. 29, 2005, which is incorporated by reference herein in its entirety.

FIELD OF THE INVENTION

The invention relates to a method and device for removing artefacts caused by patient respiration in measured blood pressure data and in particular in blood pressure data acquired invasively in the heart and/or an artery of the patient.

BACKGROUND OF THE INVENTION

In the diagnosis of cardiovascular diseases, cardiac catheterization can be a valuable tool for the cardiologist. During the procedure, the blood pressure can be invasively measured with catheters inserted into the patient's heart or major arteries, and the blood pressure waveform is measured during several heart beats.

However, the blood pressure waveform is also affected by the work of the respiratory system, inducing a low-frequency variation in the waveform. The contraction of the diaphragm compresses and decompresses the lungs and thereby varies the intra-thoracic pressure. Since the pressure measured by the catheter is referred to atmospheric pressure, rather than the actual intra-thoracic pressure, there is a cyclic variation in the observed blood pressure at the respiratory frequency, caused by the patient's respiration.

A further effect of the intra-thoracic pressure variations caused by respiration is the increase of peripheral blood vessel resistance: Increased intra-thoracic pressure will also put pressure on the arteries, which will increase the right ventricular afterload. Afterload is the load the heart must eject blood against during systole. Further, increased pressure on the veins increases the filling of the left atrium, leading to an increased left ventricular output. The net effect of all this will be, that the diastolic pressure in the ventricles will be effected more or less directly by intra-thoracic pressure, while ventricular systolic pressure will be effected by an additional cyclic variation caused by changes in afterload, preload and intra-ventricular dependencies.

In addition, the heart-rate also varies with respiration, a phenomenon called respiratory sinus arrhythmia (RSA). During inspiration, there is an increase in heart-rate, in order to keep cardiac output constant in spite of the increased pressure resistance. Hence, RSA reduces variations in cardiac output caused by respiration, but in return causes large variations in the systolic pressure in the aorta. These variations often appear slightly phase-shifted from the effect of intra-thoracic pressure variations.

The three above described effects influence blood pressure measurements and lead to inaccurate results when calculating diagnostic parameters, such as systolic pressure (SP), beginning of diastolic pressure (BDP), and end diastolic pressure (EDP).

Previous attempts to compensate for these respiratory artefacts have merely used low-pass filters in order to filter out such components oscillating at about the respiratory frequency. Such methods are disclosed for example in the article by S. A. Hoeskel, J. R. C. Jansen, J. A. Blom und J. J. Screuder: "Correction for respiration artefacts in pulmonary blood vessel signals of ventilated patients", Journal of Clinical Monitoring, 12, pages 397 to 403, 1996.

SUMMARY OF THE INVENTION

It is an object of the invention to provide an improved method for removing respiratory artefacts in blood pressure measurements.

This object is achieved by the methods according to independent and dependent claims, as well as by the device according to another independent claim. Preferred embodiments of the invention are defined in the respective dependent claims.

According to the method of an independent claim, the level of $CO_2$ in the patient's expired air is acquired as a respiratory signal during the blood pressure measurement, and the respiratory signal is used to approximate and remove the artefacts caused by patient respiration. Hence, the invention makes use of the relationship between respiration and the level of $CO_2$ in the expired air. The $CO_2$ content may be measured by a straightforward method, for example using the equipment available from Orison Systems Ltd. (see www.oridion.com). Here, the patient is connected to a cannula, e.g. nasally. Through the cannula, expired air is sampled by a pump which is placed in a bedside handheld monitor. The $CO_2$ level is analysed by a spectrometer positioned inside this monitor. Although there is a small time delay between respiration and the measured $CO_2$ content, this delay may easily be estimated and compensated for.

The respiratory signal may be used to calculate a model for the intra-thoracic pressure variations caused by respiration, and the influence on the diastolic and systolic blood pressure may be derived from the model. Hence, such pressure variations may be removed from the measured blood pressure waveform.

According to a first preferred embodiment, the level of $CO_2$ is measured over several breaths, and the respiratory frequency is extracted from the respiratory signal, preferably by identifying the end-tidal $CO_2$ level for each breath. The respiratory frequency is then used to derive a model for the respiratory artefacts, and the model is subtracted from the measured blood pressure data. Most preferred, the model is a linear Fourier combiner, e.g. a Fourier series having components at the respiratory frequency as well as higher order harmonics. The phase and amplitude of each component is adapted using an iterative algorithm, such as a recursive mean square algorithm, preferably having a forgetting factor, or a least mean square algorithm. Preferably, only first and second order harmonics, or first to third order harmonics are used. It has been shown that this method achieves even better results if only blood pressure data sampled during the diastolic period are chosen to adapt the phase and amplitude of each component. This is due to the above mentioned differences between variations in diastolic and systolic pressure. This method is particularly suitable for ventilated patients having a constant respiratory frequency.

According to a second preferred embodiment, a reference signal is generated from the measured respiratory signal, the reference signal having a pre-determined function of the same length as the measured respiratory signal, a model for the respiratory artefacts is derived from the reference signal, and the model is subtracted from the measured blood pressure data. Preferably, the model is a finite impulse response model and, most preferred, it is adapted using an iterative algorithm, such as a recursive mean square algorithm or a least mean square algorithm. A finite impulse response filter is a system in which each output is a linear combination of a finite number of input data. This method is also called "adaptive noise canceller". It is based on the consideration that the respiratory artefacts are a disturbance which is correlated to a reference signal. The relationship between the reference signal and the disturbance may be established by an adaptive filter.

Preferably, the respiratory signal is analysed for generating the reference signal, wherein the start, stop and maximum data points for each breath may be calculated. From these values, a function having the same length as the measured respiratory signal is generated.

Preferably, the method also includes a step of compensating for respiratory sinus arrhythmia. In this step, preferably an ECG signal is recorded during the blood pressure measurement, and the instantaneous heart rate during the blood pressure measurement is calculated from the ECG signal, a relative heart rate is calculated as the difference between the instantaneous heart rate and the mean heart rate, the relative heart rate is used as input to an autoregressive model with exogenous input (ARX-model) for modelling the systolic blood pressure of each heart beat, which is adapted to the measured variations from the mean systolic blood pressure data, and the adapted autoregressive model is subtracted from the measured systolic blood pressure data. Preferably, the parameters of the autoregressive model are recursively adapted in order to derive the systolic pressure artefact caused by variation in heart rate. Further, the autoregressive model is preferably subtracted from the measured systolic blood pressure data in a way that does not alter the shape of the blood pressure waveform. This may be done for example by calculating a dampening constant between the end-diastolic pressure point and the begin-diastolic pressure point surrounding the systolic pressure that is being reduced.

According to a further aspect of the invention, a method for removing artefacts caused by patient respiration in measured blood pressure data is provided in which the measured blood pressure data are decomposed into several components by means of a wavelet transform, some of the components containing largely the respiration artefacts, wherein those components are optionally processed and then subtracted from the measured blood pressure data. A wavelet is a waveform of finite length having a mean value of 0. In contrast to the Fourier analysis, in which the signal is decomposed into sinus waves of infinite length, in wavelet analysis the signal is broken into local and often irregular and asymmetric wavelets. Hence, the wavelet transform is better suited for local functions.

The wavelet transform is defined as follows:

$$CWT_x^\psi(\tau, s) = \frac{1}{\sqrt{|s|}} \int x(t)\psi\left(\frac{t-\tau}{s}\right)dt \quad (1)$$

where $\Psi$ is the transforming function, the wavelet.

By applying a wavelet of about the same form as a blood pressure curve to the measured blood pressure data, the blood pressure data can be decomposed into several components. The blood pressure curve is essentially contained in one or two components, while the respiratory artefacts will fall under decomposition levels of higher scale (lower frequency). Hence, these components may be subtracted from the measured data in order to remove respiration artefacts.

The invention is further directed to a device for acquiring and correcting blood pressure data, having a catheter insertable into the heart or an artery for measuring blood pressure, the device further containing a sensor for measuring the level of $CO_2$ in the patient's expired air as a respiratory signal, and a data processing module for removing artefacts in the measured blood pressure data, wherein the data processing module is adapted to use the respiratory signal to approximate and to remove the artefacts caused by patient respiration. Preferably, the device is adapted to carry out the above described method.

BRIEF DESCRIPTION OF THE DRAWINGS

Preferred embodiments of the invention shall now be described with reference to the accompanying drawings, in which.

DETAILED DESCRIPTION OF THE DRAWINGS

Figure 1:
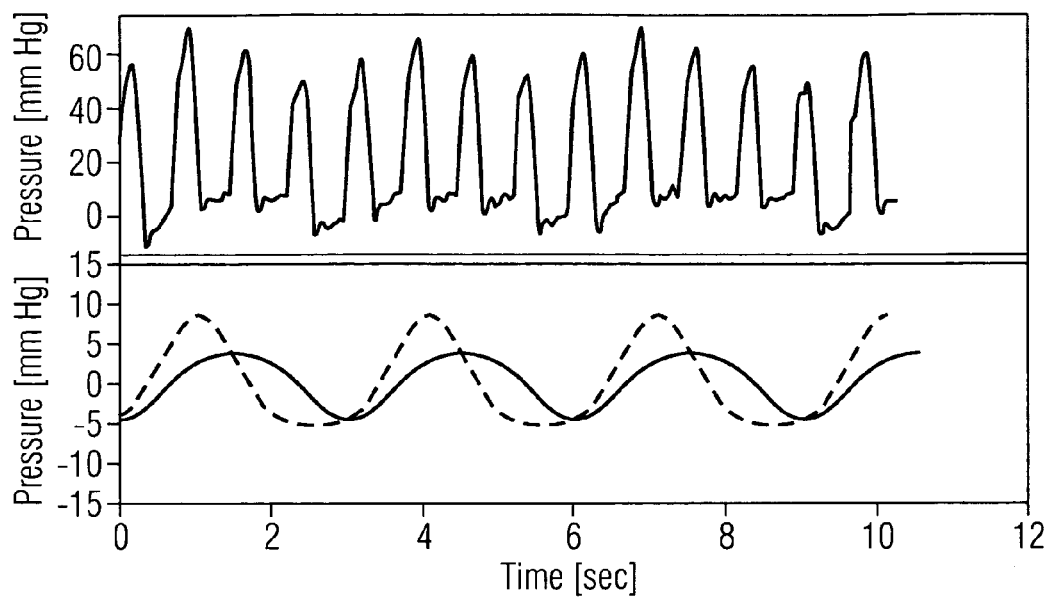
FIG. 1 shows a graph of measured blood pressure signal versus time, as well as estimated artefacts in diastolic and systolic pressure.

To visualize the respiratory artefacts in measured blood pressure, FIG. 1 depicts the measured blood pressure in the right ventricle, as well as the estimated respiratory artefacts. The solid curve shows artefacts considered as variations in diastolic pressure, and the dashed curve artefacts considered as variations in systolic pressure.

Figure 2:
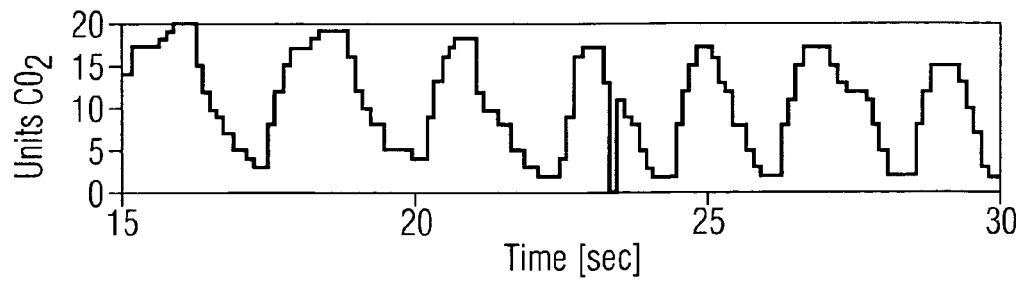
FIG. 2 shows a graph of the measured $CO_2$ level versus time.

FIG. 2 shows the respiratory signal which is a signal of the amount of $CO_2$ in expired air.

Figure 3:
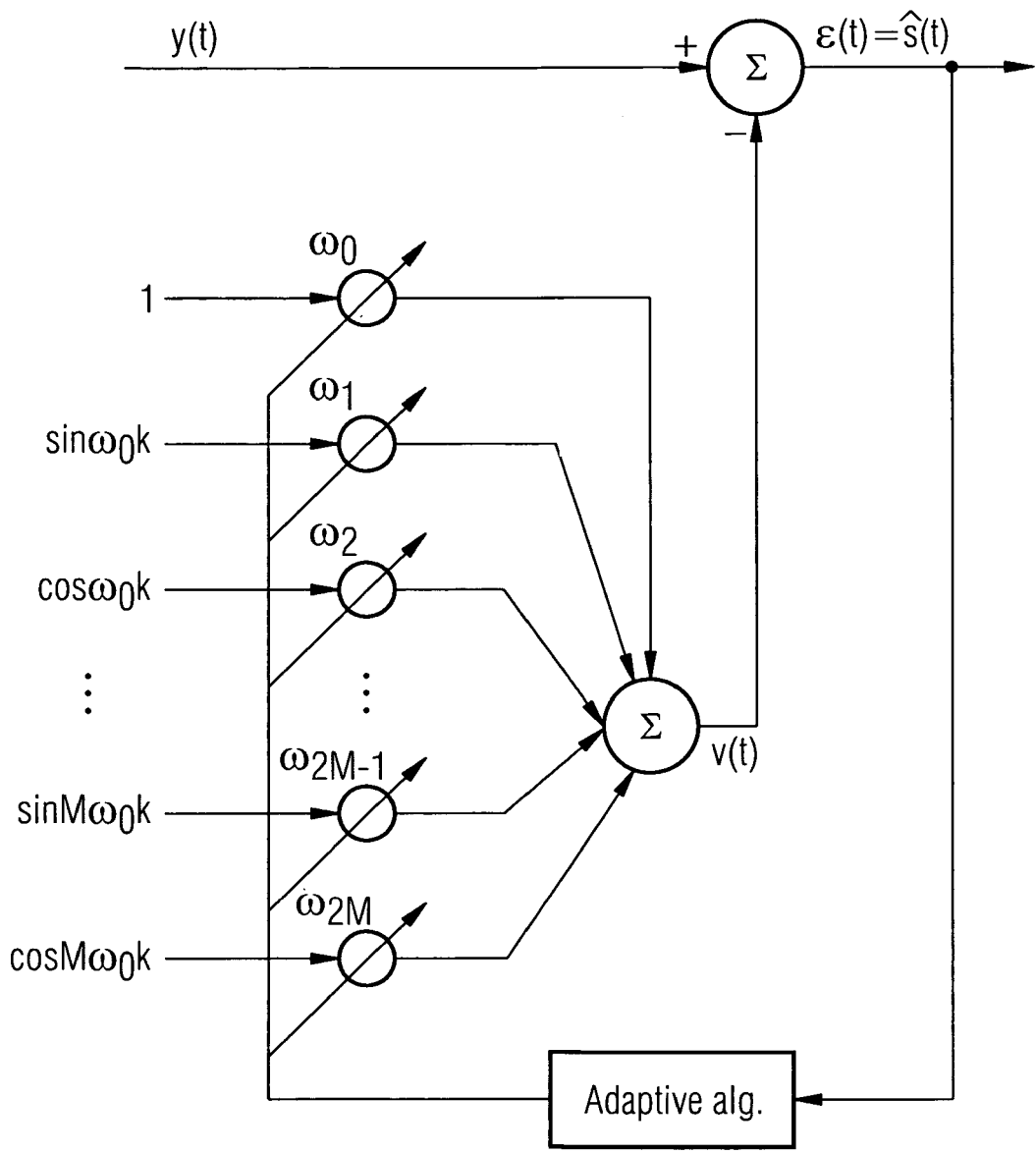
FIG. 3 shows a flow chart of a first embodiment of the method according to the invention.

With regard to FIG. 3, the first embodiment of the invention shall now be explained in detail. The measured blood pressure signal y(t) can be described as the correct blood pressure s(t) and a disturbance v(t) caused by respiration:

$$y(t)=s(t)+v(t) \quad (2)$$

The disturbance v(t) may be described as a series of sinusoids, called a dynamic Fourier series model. The coefficients of this series are dynamically adapted. This concept is called an adaptive Fourier linear combiner. A flow chart of an adapted Fourier linear combiner is shown in FIG. 3. The fundamental frequency of this model is the respiratory frequency $\omega_0$, which can be extracted from the respiratory signal and used to model the respiratory disturbance in the blood pressure as $$\hat{v}(w, t) = \omega_0(t) + \sum_{k=1}^{M} [\omega_{2k-1}(t)\sin(\omega_0 tk) + \omega_{2k}(t)\cos(\omega_0 tk)] \quad (2)$$

$$w(t) = [\omega_0(t), \omega_1(t), \ldots, \omega_{2M}(t)]^T \quad (3)$$

An approximation to the correct blood pressure s(t) is then:

$$\hat{s}(t)=y(t)-\hat{v}(w,t) \quad (4)$$

The phase and the amplitude of a respiratory signal v(w,t) is estimated when adapting equation (4) by adjusting the weights w using an adaptive algorithm. Different adaptive algorithms can be used such as the recursive mean spare algorithm or the least mean square algorithm.

This system acts as a kind of adaptive band stop filter for the respiratory frequency $\omega_0$ and its M harmonics.

If the number of coefficients is set too high, components from the correct blood pressure waveform may be described by the Fourier series and therefore falsely removed. To ensure that this does not happen, the length of the series is preferably set so that the highest frequency that can be described by the series is lower than the heart rate. If the heart rate is $\omega_1$, this gives a maximum limit for $$M \leq \frac{\omega_1}{\omega_0} \quad (5)$$

rounded downwards to the closest integer value. In the experiments, M=2 was enough to give a good result. However, third, fourth and higher order harmonics may also be included.

Preferably, only such blood pressure data measured during the diastolic phase are used. This leads to a faster convergence of the algorithm.

Figure 4:
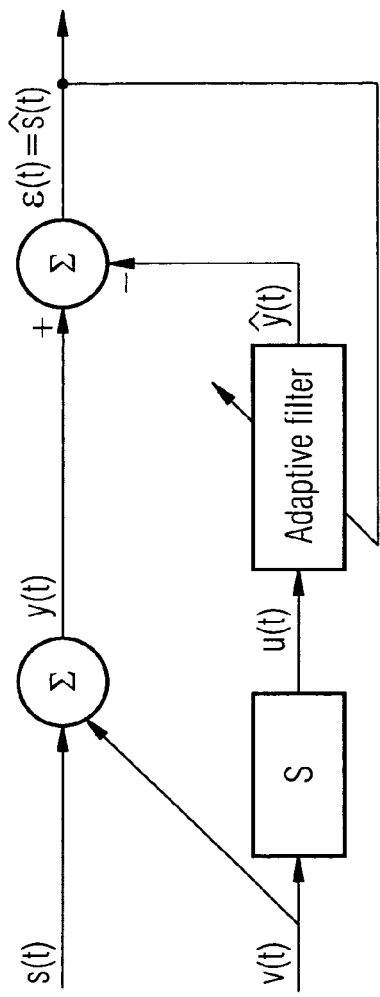
FIG. 4 shows a flow chart of a second embodiment of the method according to the invention.

With reference to FIG. 4, a second embodiment of the method according to the invention shall now be described. In this so-called "adaptive noise canceller", a reference signal u(t) for the disturbance v(t) is calculated which is highly correlated with the disturbance. The output of the adaptive filter ŷ(t) will be subtracted from the measured signal y(t) to form an error signal ϵ(t) which is used to update the filter. This would be an estimate to s(t), the correct blood pressure.

Figure 5:
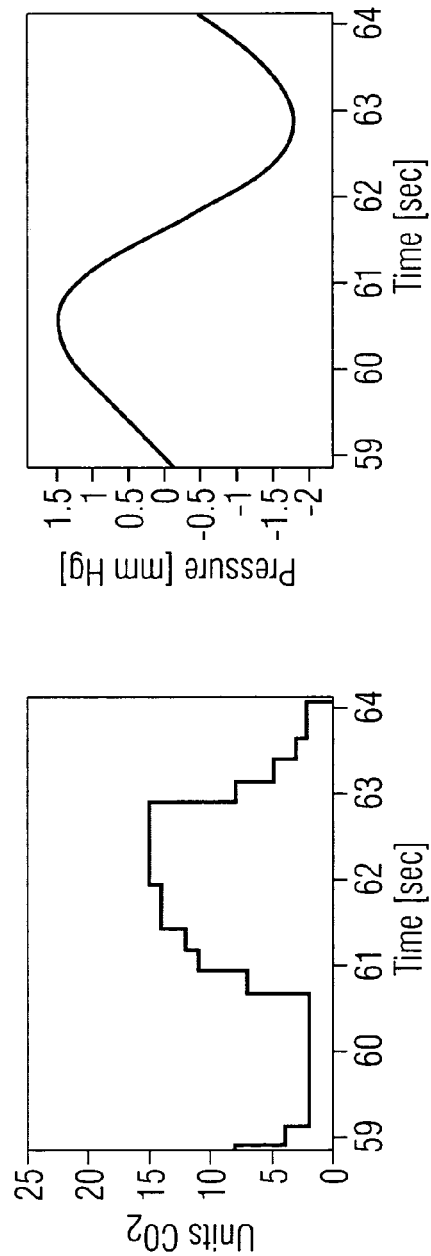
FIG. 5 shows a graph of measured $CO_2$ level and a reference signal.

However, this method cannot be used directly in this case, because there is no correct reference signal for the disturbance. The measured respiratory signal is a measurement of the level of $CO_2$, not the intra-thoracic pressure, and must first be processed before it can be used as a reference. This difference is demonstrated by FIG. 5, which shows the measured respiratory signal on the left and the corresponding actual artefact, approximated from the blood pressure signal, on the right.

Therefore, from the acquired respiratory signal, a reference signal is generated. To generate this new signal, the measured respiratory signal is analysed and the start, stop, and a maximum point for each breath is calculated. From the calculated values, a function having the same length as the original is generated, preferably by adjusting a sinus-curve.

Preferably, the reference signal has the following formula:

$$p(t) = \begin{cases} A_{insp}\sin(t), & 0 \leq t < \pi/2 \\ A_{insp}\left(\sin(t) - (\sin(t) - 1)\frac{1 + A_{exp}}{2}\right), & \pi/2 \leq t < 3\pi/2 \\ -A_{exp}\sin(t), & 3\pi/2 \leq t < 2\pi \end{cases} \quad (6)$$

where $A_{exp}$ is the expected change in pressure during an expiration compared to the inspiration $A_{insp}$. If the patient is free breathing, the value of $A_{insp}$ is assumed to be about minus $A_{exp}$, meaning the change during expiration is the opposite of inspiration. For a mechanically ventilated patient, $A_{exp}$ can be assumed to be around 0.1 $A_{insp}$ indicating a constant positive pressure.

The change in amplitude between breath is adjusted by the variable $A_{insp}$ which is set to the maximum point $R_{max}$.

When a reference signal has been created, the actual compensation can begin. The reference signal is thereby used to model an approximation to the respiratory artefacts y(t). This may be done by describing y(t) as a finite impulse response model defined as $$\hat{y}(t) = w_1(t)u(t-1) + \ldots + w_m(t)u(t-m) + e(t) \quad (6)$$

The filter weights $w_1 \ldots w_m$ can then be updated according to a normalized mean square or a recursive mean square algorithm.

If the low-frequency variations in the diastolic pressure appear as a phase-shifted version in systolic pressure (see FIG. 1) a normal filter approach will not give a correct result. To counter this problem, only the end-diastolic pressure is used for updating the adaptive algorithm. This ensures that the correct respiratory artefact is reduced.

In order to compensate for artefacts caused by RSA a further method step is suggested. After removing the artefacts caused by intra-thoracic pressure variations by one of the above described methods, the remaining artefacts may be removed as follows:

First, a measure for RSA must be found. This is done by using an ECG-signal to calculate the instantaneous heart rate over the measurement period. If an ECG is taken over several heart beats, a mean heart rate may be calculated as well. This is used to calculate the relative heart rate r, defined as the difference of the actual heart rate to the mean rate over a given time window.

The compensation method then consists in calculating a compensation according to the change in instantaneous heart rate. This is done by letting the remaining systolic pressure variations be modelled as an ARX-model (autoregressive model with exogenous input) with input r(n), corresponding to the change in heart rate. If the systolic pressure for the current heart beat n is denoted $p_{sp}(n)$, the variation from the mean systolic pressure over 1 heart beats may be denoted as $p_{SPVar}(n)$.

The ARX-model can then be written as $$\hat{p}_{SPVar}(n) + a_1(n)\hat{p}_{SPVar}(n-1) + \ldots + a_N(n)$$
$$\hat{p}_{SPVar}(n-N) = b_1(n)r(n-1) + \ldots + b_m(n)r(n-M) + e(n) \quad (7)$$

An adaptive algorithm will update the parameters recursively in a similar way as the above mentioned FIR-model to minimize the model error between the actual and the calculated $p_{SPVar}(n)$. The forgetting factor may be set to about 0.95, i.e. about 20 beats are remembered, which gives a fast convergence. The output $p_{SPVar}(n)$ is the systolic pressure originating from heart rate variations. That is the amount that should be removed from the measured systolic pressure $p_{SP}(n)$.

Figure 6:
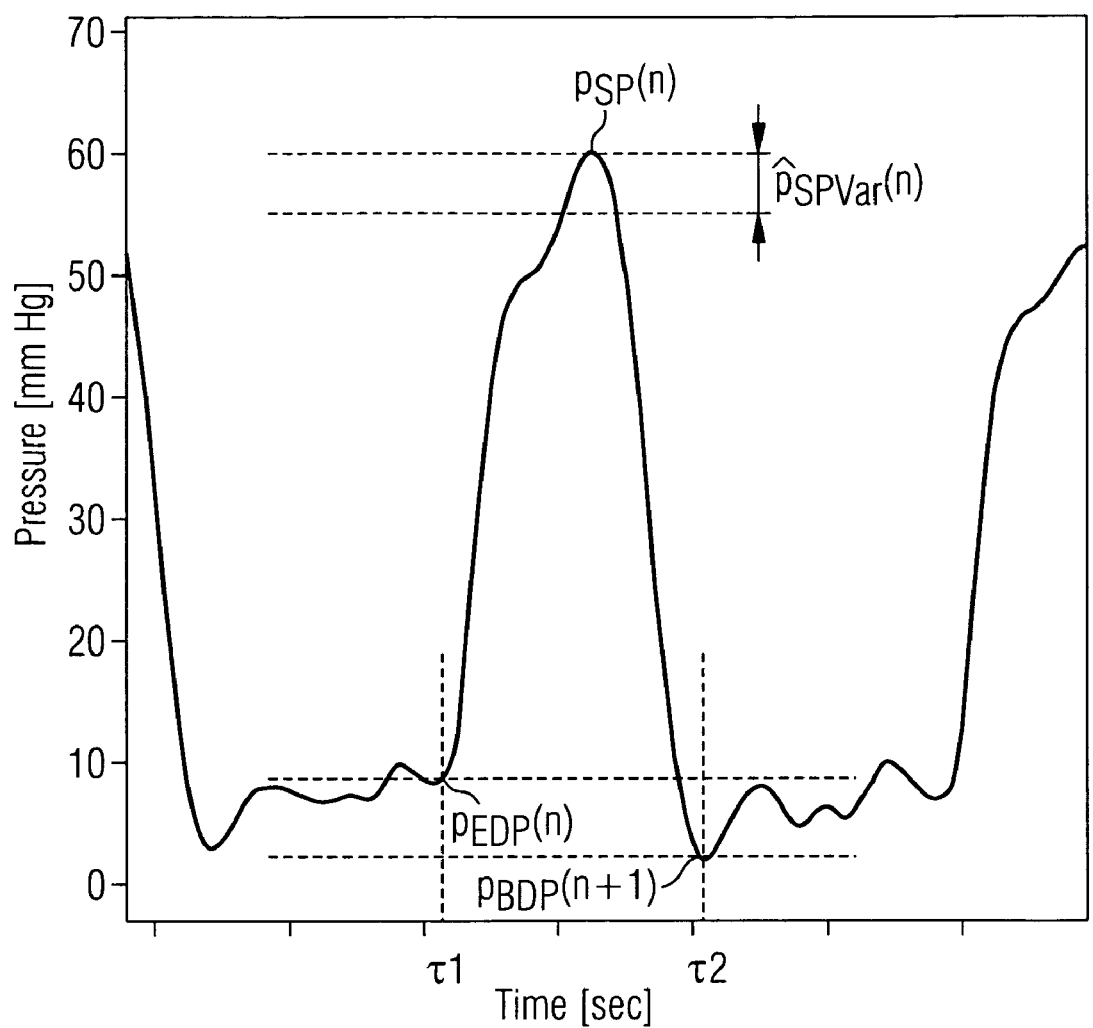
FIG. 6 shows the waveform of a heart beat to be compensated.

This should preferably done in a way that the shape of the pressure waveform will remain the same. To do this, a dampening constant is calculated between the end-diastolic pressure point $p_{EDP}(n)$ and the begin-diastolic pressure point $p_{BDP}(n+1)$ surrounding the systolic pressure $p_{SP}(n)$ that is being reduced. This is illustrated in FIG. 6. A dampening constant d(n) is then set so the systolic pressure $p_{SP}(n)$ is reduced by $p_{SPVar}(n)$:

$$d(n) = \frac{p_{SP}(n) - b(n) - \hat{p}_{SPVar}(n)}{p_{SP}(n) - b(n)} \quad (8)$$

Every pressure sample p(t) between $\tau_1$ und $\tau_2$ is altered in a way that reduces the systolic pressure in a smooth way, such that the shape of the waveform will be preserved.

The invention claimed is:

1. A method for removing artifacts caused by patient respiration in measured blood pressure data acquired invasively in the heart or an artery of the patient, comprising:
   acquiring the level of CO2 in the patient's expired air as a respiratory signal during the blood pressure measurement by a sensor;
   using the respiratory signal to approximate the artifacts caused by patient respiration by a data processing unit; and
   removing the artifacts based on the respiratory signal by the data processing unit.

2. The method according to claim 1, further comprising after the $CO_2$ acquiring step;
   generating a reference signal from the measured respiratory signal, wherein the reference signal has a predetermined function of the same length at the measured respiratory signal;
   deriving a model for the respiratory artifacts from the reference signal; and
   subtracting the model from the measured blood pressure data.

3. The method according to claim 2, wherein the model deriving step further comprises, deriving a finite impulse response model and, adapting the model using an iterative algorithm.

4. The method according to claim 3, wherein the adapting step comprises, using a Recursive Mean Square Algorithm.

5. The method according to claim 4, wherein the adapting step comprises, adapting the finite impulse response model by choosing only blood pressure data sampled during the diastolic period.

6. The method according to claims 2, wherein the reference signal generating step comprises, analyzing the respiratory signal for generating the reference signal, and wherein the analyzing step comprises calculating the start, stop and maximum data points for each breath.

7. The method according to claim 1, further comprising a step of compensating for Respiratory Sinus Arrhythmia.

8. The method according to claim 7, the compensating step further comprising:
   recording an ECG signal during the blood pressure measuring step;
   calculating the instantaneous heart rate during the blood pressure measurement from the ECG signal;
   calculating a relative heart rate as the difference between the instantaneous heart rate and the mean heart rate;
   using the relative heart rate as input to an autoregressive model with exogenous input for modeling the systolic blood pressure of each heart beat;
   adapting the model to the variations in the measured systolic blood pressure data; and
   subtracting the adapted autoregressive model from the measured systolic blood pressure data.

9. The method according to claim 8, wherein the model subtracting step comprises, subtracting the autoregressive model from the measured systolic blood pressure data in a manner so as to not alter the shape of the blood pressure waveform.

* * * * *